United States Patent [19]

Murphy

[11] Patent Number: 5,013,156
[45] Date of Patent: May 7, 1991

[54] OPTICAL DENSITY MEASUREMENT APPARATUS IN THE CONTEXT OF LABELING AND OTHER DEVICES

[75] Inventor: William J. Murphy, South Acworth, N.H.

[73] Assignee: IMTEC, Inc., Bellows Falls, Vt.

[21] Appl. No.: 328,286

[22] Filed: Mar. 24, 1989

[51] Int. Cl.$^5$ ............... G01N 21/55; G01N 21/59; G01N 21/86

[52] U.S. Cl. .................. 356/432; 250/205; 250/548; 250/557; 356/434; 356/445

[58] Field of Search ............ 356/432, 434, 443, 445, 356/447, 448; 250/205, 548, 557

[56] References Cited

U.S. PATENT DOCUMENTS

| | | | |
|---|---|---|---|
| 2,080,292 | 5/1937 | Webber | 250/548 X |
| 3,542,479 | 11/1970 | Sibalis | 356/445 X |
| 4,300,689 | 11/1981 | Franklin et al. | 356/407 X |
| 4,342,906 | 8/1982 | Hyatt | 250/205 |

*Primary Examiner*—Vincent P. McGraw
*Attorney, Agent, or Firm*—Robert Shaw

[57] ABSTRACT

A system to apply a bar-code label or the like upon a product or to apply a protective laminate strip or the like upon a bar-code label or the like which is already in place upon a product. The label or the protective laminate strip first is removed from a moving carrier and applied to an applicator head which, in turn, applies the label on the product or the protective laminate strip very precisely onto the label. The relative positions of the applicator head and the label, for example, are predetermined. It remains to establish the moving forward edge of the bar-code label or the protective laminate strip to be stripped from the moving carrier so that the either can be accurately placed on the applicator head, a particularly vexing problem in view of the fact that transmissivity, usually, or reflectivity of all the films involved, typically, have closely related optical characteristics. The system discloses uses pulse-width-modulated techniques (PWM) and duty cycle which overcome inherent problems that arise from those optical characteristics, e.g., wandering of sensing circuitry over time or due to temperature, moisture and the like. Hence the high sensitivity and stability needed for such purposes are provided. The system disclosed uses digital counting techniques with their stability, particularly in the context of duty cycle. The concepts herein disclosed are framed in the context of labeling devices but are broader.

25 Claims, 7 Drawing Sheets

OPTICAL DENSITY MEASUREMENT APPARATUS IN THE CONTEXT OF LABELING AND OTHER DEVICES

The present invention relates to systems for labeling which permit very precise positioning of labels onto a surface, as well as protective covers upon the labels, the labels serving, for example, as a mechanism to identify a product to which the label is secured and the protective covers providing mechanical and other protection for the label. (The major emphasis herein is that of applying a laminate strip as a protective cover upon a bar code or other label previously applied to a product.)

There are many requirements for positioning of labels or other thin films onto a surface. One particularly vexing requirement is the labeling of printed circuit ("pc") cards. With the ever increasing demand for higher package density and smaller size, space on the circuit card surface becomes more limited. Competitive pressures mandate the use of increasing automation in the manufacturing process, which usually results in the need to apply labels to the card at the beginning of the assembly process. These labels must be machine readable, contain significant amounts of information for use in subsequent steps of the process and must survive all of the environmental conditions such as wave soldering and vapor degreasing to which they are subjected throughout the process. The small size and high density requirements of such labels demand accurate placement on the pc card. The severe environmental conditions usually dictate the use of laminating film over the printed surface of the label in order to maintain legibility.

In some cases, information can simply be preprinted on the card prior to assembly. This technique, however, is quite limited and precludes the use of variable information such as lot numbers, serialization, date codes, batch assembly identifiers, etc. The most general solution involves printing and applying a label that will withstand the environment at the time that the card enters the assembly process. In some cases, labels can be printed on continuous label stock and then covered with a laminating film. The composite label thus formed can be cut to size by a butt cutter and applied to the surface to be labeled. A problem that arises with this approach is that the subsequent steps of laminating and cutting result in a queue of labels between the print point and the application point so that the label being printed is not the label being applied. There are cases where the queue thus formed presents no inherent problem and the butt-cut laminator provides an acceptable solution.

In those cases wherein the queue does present a problem, one solution is to use labels which are previously die cut to size and applied on a continuous backing. The spacing between labels on the backing is sufficient to allow a label to be printed and stripped from the backing onto an applicator head without causing the next label to advance beyond the print point. With this solution, labels are printed and applied and then subsequently laminated as a second step. The laminating step can be accomplished either by using a separate applicator that is supplied with a roll of die cut laminate conforming to the label size or by supplying the printer-applicator with a composite label stock that consists of alternating strips of label stock and laminate. With such a stock, the printer-applicator first prints the label on the label stock, strips the label onto the applicator head, applies the label to the surface, strips the laminate film onto the applicator head and applies the laminate to the surface. This cycle is then repeated for each label to be printed, but registration of the laminate film upon the label is a non-trivial problem.

The detection apparatus described in this disclosure has utility in registering printed labels accurately in that it can easily detect the location of a reference edge of the printed label and feed this information to the control system of an applicator which will subsequently apply the label. Label material is normally relatively dense optically compared to the backing material which serves to transport the label so that a fairly good contrast ratio exists between the label plus backing and the backing itself. The detector system described enchances placement accuracy, but is not always necessary for detection per se.

Laminating film presents a much more difficult detection problem in that almost by definition the film itself must be optically quite transparent at the wavelengths which will be used in reading the labels. In the general case, the printed label contains both machine readable information such as bar code and human readable information such as alphanumeric characters. Bar code information is oftentimes read with infrared scanners whereas the human readable text is obviously read with visible light. These requirements dictate the use of laminating films with relatively nigh optical transmissivity.

In order to detect the laminating film on the backing accurately, a detection system of high sensitivity and stability is required. Further, in order to discriminate between labels and laminate in the case of the composite label stock, high accuracy and resolution as well as wide range is required. The invention disclosed herein meets all these requirements.

Accordingly, it is an object of the invention to provide a labeling system which is operable to apply a precisely positioned label (e.g., a bar-code label) onto a product in a mechanism in which both the label and the product are moved into position just prior to such application.

A still further object is to provide a system that has characteristically high stability and sensitivity of a scale required for present purposes.

Another object is to provide a system which can apply a precisely accurately physically spaced protective laminate strip over the label, just previously placed on a product or a label so placed at an earlier time.

Still another object is to provide a system to accomplish the foregoing despite typical changes usually encountered in such systems due, for example, to changes in detecting circuitry usually used because of temperature change, for example.

Still another object is to provide a system which requires minimal maintenance, which will operate reliably over long time periods despite adverse environmental conditions, which will operate in the context of wave energy other than visible light, and which can be employed in many other applications where sensing or a material property is required.

A further object is to provide an acceptable economic way to provide the foregoing.

These and still further objects are addressed hereinafter.

The foregoing objects are achieved, generally, in optical density measurement apparatus typically operable to measure the transverse optical density or other physical property of a composite material, that includes a light or other radiation source whose spectral characteristics are generally matched to the material to be measured, positioned to direct radiation onto the composite material which effects a change in the intensity of the radiation; a detector whose optical characteristics are generally matched to the light source, positioned to detect the radiation after interaction with the composite material and operable generate a voltage signal indicative of the intensity level of the detected radiation; a control circuit connected to energize the light source and being interconnected to receive the voltage signal, the performance characteristics of the control circuit being chosen such that the control circuit is operable in response to the voltage signal to modify the average output of the light source and maintain the voltage output of the detector substantially constant, the control circuit being pulse-width modulated (PWM) to effect modification of the average output of the light source to maintain substantially constant output from the detector by varying the average output from the light source in response to the voltage signal In this way errors which otherwise would occur, due, for example, to non-linearity of circuits elements and drift over time and temperature, are eliminated. The optical density apparatus typically is part of a system that further includes a mechanism to determine changes in the optical density and to react in response to changes in the optical density. The system typically further includes an applicator that is actuated in response to occurrence of an edge between materials of differing optical density (or reflectivity) and which is connected to receive actuation signal representative of changes in optical density (or other characteristics) of the composite and is actuated thereby.

The invention is hereinafter described with reference to the accompanying drawing in which:

FIG. 10 is a side diagrammatic view of a portion of a mechanism to apply a bar-graph label or the like upon an object and then to apply a laminate strip upon the bar-graph label or the like; and FIG. 11 is a block diagram of a system to apply a label or a protective cover of the like upon a label or the like.

Figure 1:
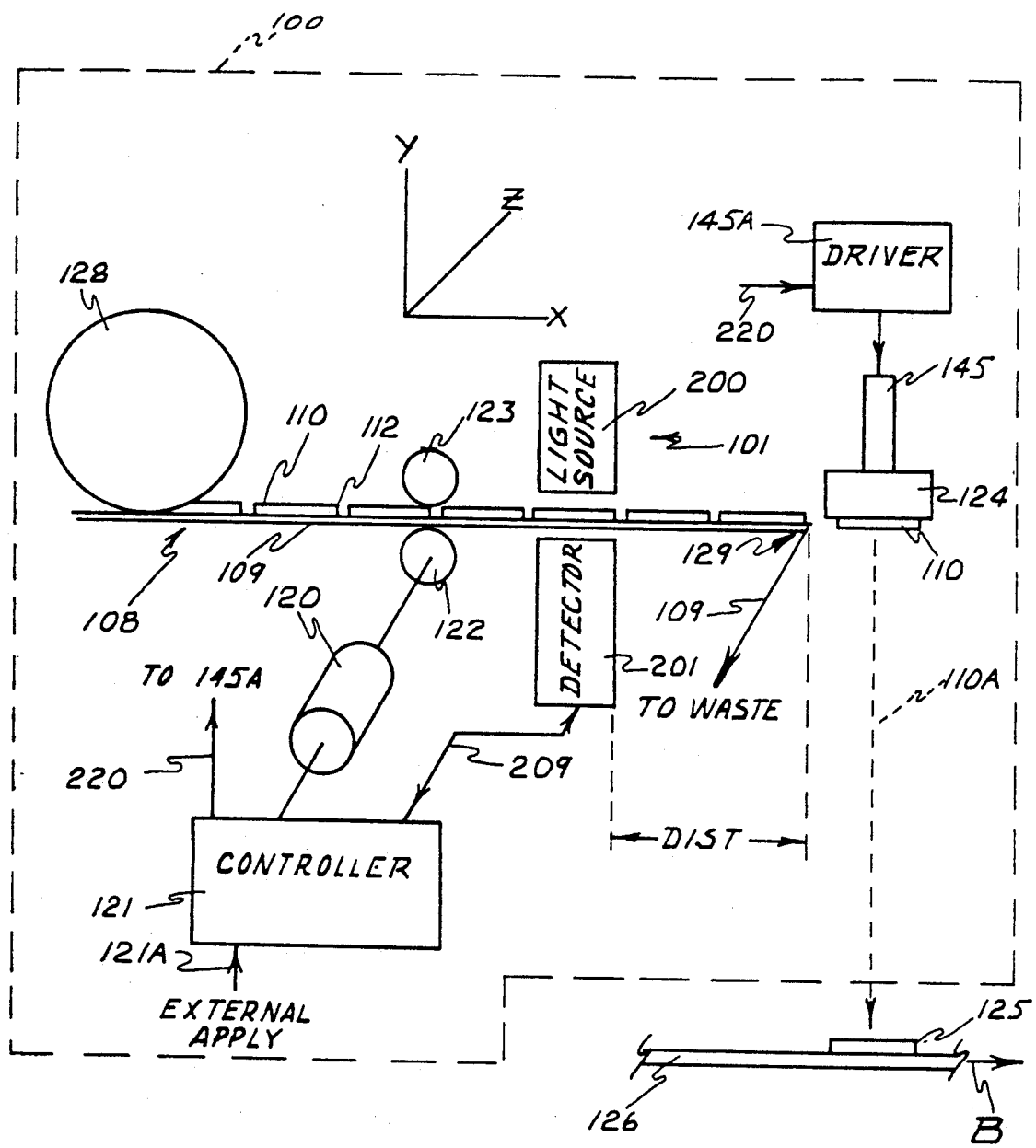
FIG. 1 is a diagrammatic representation of a system that functions to apply a laminar strip onto a product, using signals derived from a control system that includes a detector system that physically locates the laminar strip in space relative to the product.

The purpose of the system labeled 100 in FIG. 1 is to strip a protective laminate strip 110 (or laminating film) from the backing tape designated 109 (FIG. 2) of a composite material 108 and to deposit the laminate strip 110 (as indicated by a broken line 110A in FIG. 1) upon a bar-code label or the like 125 disposed on an object 126. The arrows A and B point in direction of motion respectively of the tape 108 and the object 126. The system 100, according to the present inventive concepts, is structured to permit very precise placement of the protective laminate 110 (which typically is a rectangular pad) upon the label 125 (which typically is also a rectangular pad).

Figure 2:
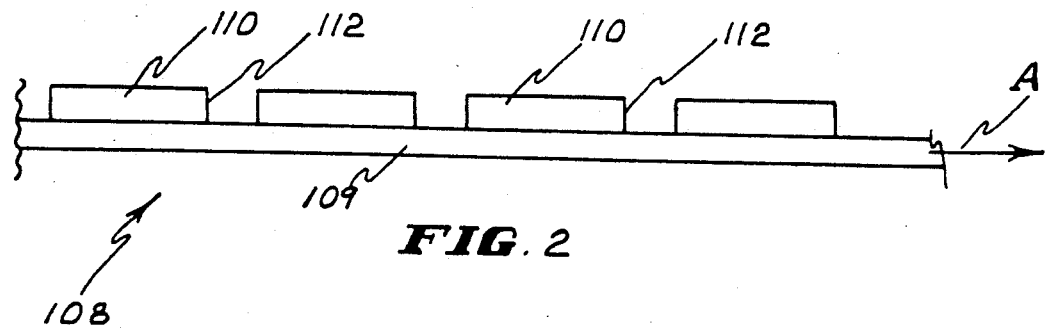
FIG. 2 is a side view of a composite material that includes a backing tape and a series of laminar strips which are stripped from the backing tape and applied onto a label.

Although the terms used herein are discussed above and later, it may be helpful to discuss several here. With reference to FIGS. 1 and 2, the printed label, (i.e., that which is to be mechanically protected) is the printed label 125; the protective coating applied onto the label 125 is the laminating film 110 (which is a rectangular strip or pad). The backing strip 109 is a translucent or transparent strip and the object marked 126 i FIG. 1 is a product to be identified (e.g., a pc board). For the system 100 to perform its needed function, it is necessary that the position of the edge marked 112 of the protective laminate strip 110 be physically established in the X-Y plane and relative to the physical position of the label 125 Once that is done, it remains to apply a strip 110 onto and upon a label 125. The physical correspondence (or registration) in the X-direction in FIG. 1 between the label 125 (which is to be protected) and the laminate strip 110 (which is the protecting mechanism), addressed here and solved, is that of locating the fast-moving (X-direction) laminate 110 relative to the X-direction position (in real time) of the label 125 and depositing the laminate strip upon and in protective relationship to the label 125. It should be here noted that machines that are operable to strip a printed label or the like from a carrier (e.g., the carrier 109), are commercially available, being marketed by IMTEC, Inc., Bellows Falls, Vt., for example. The present invention adds to available technology a way to effect very precise positioning of a protective laminate strip 110 (stripped from a moving carrier 109) onto a printed label 125 (disposed on a moving product 126), as further discussed herein. The foregoing important aspects of this invention and structures are now approached in detail.

The purpose of the system labeled 101 in FIG. 1 is to detect the edge 112 of the laminate strip 110. The material 108 shown in FIG. 2 is a composite that includes the backing tape 109 and a series of precut laminate films 110. The purpose of the system labeled 100 in FIG. 1 is to apply a laminating film 110 over the label 125 that was previously applied to the object 126 (e.g., a printed circuit card, as indicated by the broken line 110A in FIG. 1). It is assumed that the object 126 can be accurately positioned under the applicator system 124 using standard techniques known to those skilled in the art.

The system 100 includes a supply of precut laminate films 110 from a supply 128 (e.g., a roll or fanfold stack) consisting of the backing 109 and the film 110, as described above. A controller 121 (e.g., a microprocessor system) is commanded by an external signal APPLY 121A to apply the laminate film 110 on top of the label 125 that has been positioned under an apply head 124 by other external means. The controller 121 has been previously programmed to know the exact distance (labeled DIST in FIG. 1) between the detector 101 and a stripper bar 129. The controller 121 actuates a position controlling motor 120 in FIG. 1 (e.g., a stepping motor) to drive a capstan 122 and a pressure roller 123 in such a way as to advance the laminate stock 108 towards the applicator head 124. As the stock advances, the laminate film 110 is stripped from the backing 109 by the stripper bar 129 and is positioned on the applicator head 124. In order to register the laminate 110 onto the head 124 accurately, the controller 121 uses information from the detector 101 to determine the exact location of the laminate edge 112 as the laminate 110 passes through the detector 101. This information, coupled with the knowledge of the detector to strip point distance (DIST), allows the controller 121 to advance the position controlling motor 120 and hence the laminate stock 108 exactly the right amount to position the laminate film 110 onto the head 124. Once the laminate film 110 is properly registered onto the head 124, the controller 121 causes the applicator head 124 to advance out and apply the laminate 110 over the label 125 by a driver 145A which actuates a shaft 145 to move the head 124 downward in FIG. 1, as known in this art.

As stated in the background discussion above, detection of the laminating film 110 is difficult since the film 110 itself must be quite transparent optically at the wavelengths used to read the label over which the laminate is placed. Conventional techniques of a cost, scale and complexity suitable for the intended application are either insufficiently sensitive or stable for reliable and precise operation. The purpose of the detector 101 is to provide a mechanism for measuring small differences in optical density reliably, accurately and inexpensively.

Figure 3:
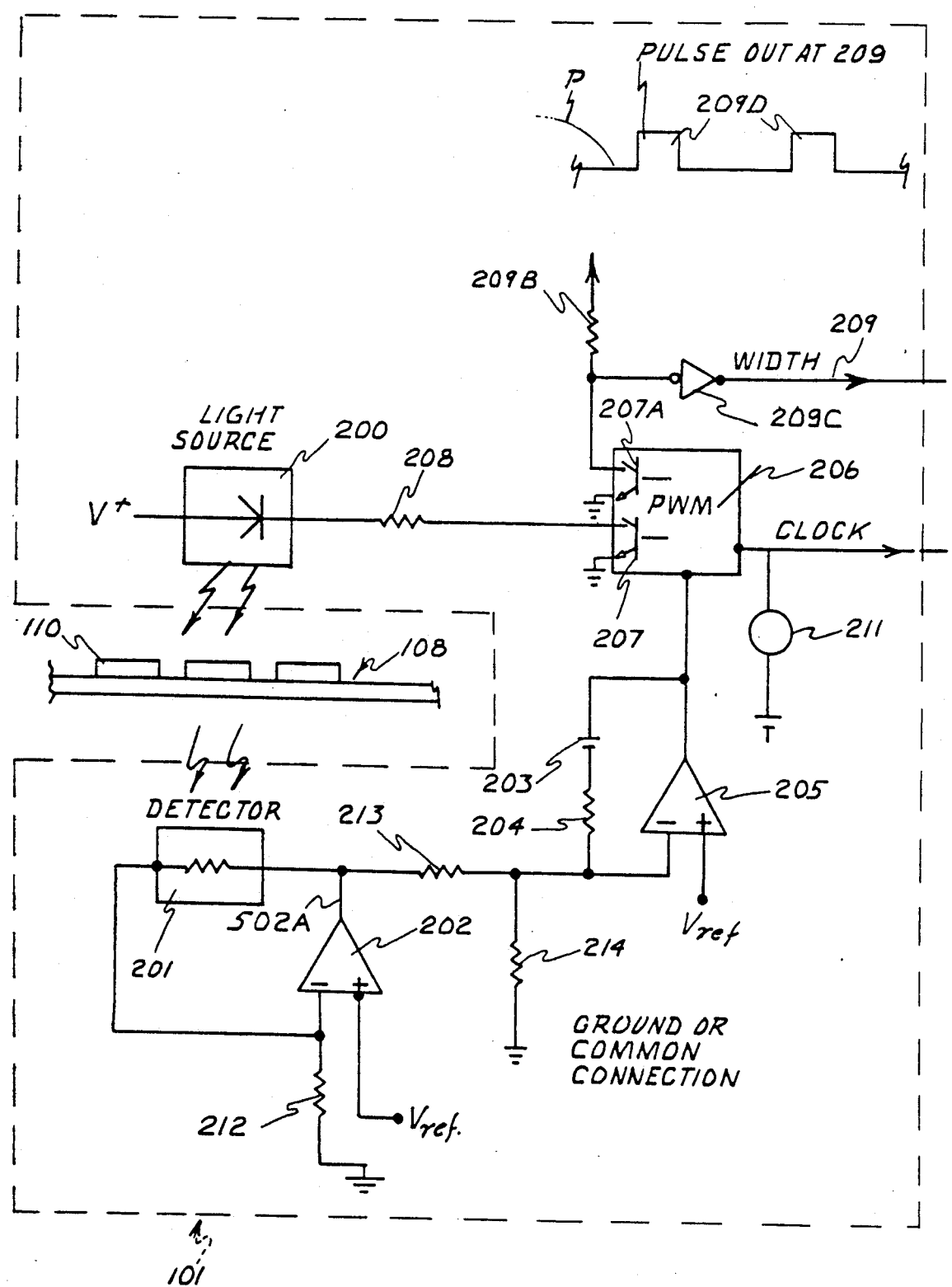
FIG. 3 is a schematic representation of a typical detector system in the circuitry of FIG. 1.

The detector 101 includes a light source 200 in FIG. 3. The light source 200 may be any light source that can be modulated in such a way as to produce an average light output that is proportional to the peak output times the duty cycle. The light source 200 is one whose spectral characteristics are matched to the material to be measured (that is, the composite 108 here); the light source 200 is positioned to direct radiation onto the composite material 108 which effects a change in the intensity of the radiation, for purposes herein disclosed. Light sources of this nature include gas discharge tubes, light emitting diodes, electro-luminescent devices, etc. To a lesser extent, incandescent filament sources may be used. For the discussion below, a light emitting diode source will be assumed, but this limitation is not restrictive. The light source 200 in FIG. 3 is driven by the output of a pulse-width modulator 206 through a suitable driver 207 shown, for example, in FIG. 3 as a transistor. During the time that the driver 207 is turned on, electric current flows through the light source 200 thereby producing a pulse of light. The peak magnitude of the current and hence the peak magnitude of the light output from the light source 200 is essentially determined by a resistor 208.

The PWM 206 may take various forms, e.g., a conventional switching regulator-modulator chip such as TL-495 of Texas Instrument which incorporates the oscillator 211, an operational amplifier 205, the modulator 206 and the uncommitted output transistors 207 and 207A, as well as the regulated reference $V_{ref}$.

In the example, the light source 200 is arranged in such a way as to direct light through the composite film 108 onto a detector 201. The detector 201 may be any photo detector whose spectral characteristics and speed of response are compatible with the light source 200 and films to be measured. Such detectors include photoresistors (e.g., CdS or CdSe photocells), photodiodes, phototransistors, etc. The embodiment shown uses a photoresistor, but this use is not restrictive.

The detector 201 is connected in the feedback loop of the potentiometric operational amplifier 202 to produce an output voltage that is proportional to the detector resistance or inversely proportional to the light falling on the detector 201, by a resistive network 213 and 214 where it is compared with the reference voltage $V_{ref}$ by the operational amplifier 205. The difference between the divided output of the amplifier 202 and the reference voltage $V_{ref}$ in FIG. 3 is amplified by the operational amplifier 205 and is used to control the pulse width of the pulse width modulator 206. The clock rate of the pulse width modulator 206 is determined by a fixed frequency oscillator 211. The clock rate is adjusted to be several times higher than the response frequency of the overall detector system. The output pulse of the pulse width modulator 206, in turn, drives the light source 200, as discussed above.

The action of the connection described above is such as to cause the pulse width of the modulator 206 to adjust to a value just sufficient to maintain the output of the photodetector 201 at a level that causes the divided output of the operational amplifier 202 to be equal to the reference voltage $V_{ref}$. Any change in the light impinging on the photodetector 201 will result in a change of the pulse width from the modulator 206 that is just sufficient to restore the photodetector 201 to its reference value. The feedback elements marked 203 and 204 are chosen to stablilize the overall feedback loop formed by the modulator 206, the light source 200, the detector 201 and amplifying the circuitry 202 and 205.

Figure 4:
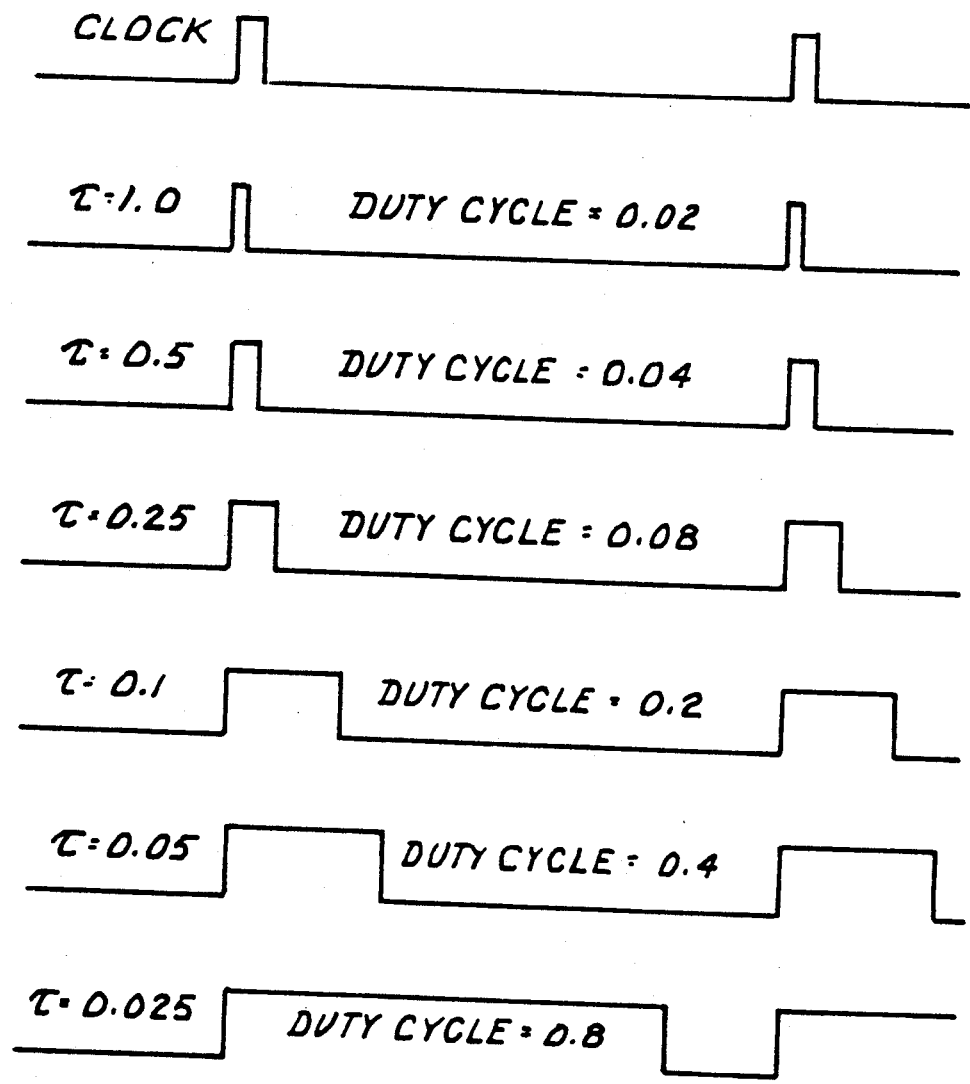
FIG. 4 shows representations of electrical pulses at 209 in FIG. 3, representative of pulse duty cycle versus transmissivity.

As material of differing optical density is inserted between the light source 200 and the detector 201, the pulse width of the modulator 206 is automatically adjusted to a value just sufficient to maintain the detector output at its reference value. The pulse width output thus serves as a measurement of the optical density of the material between the light source 200 and the detector 201. This output is shown as a signal WIDTH at 209; see pulses marked 209D in FIG. 3. FIG. 4 shows typical timing diagrams or duty cycle for materials of differing optical transmissivity Additional understanding of the operation of the detector system described above can be gained by considering the equations of operation of the system. For the transmissive case, if a film of material is irradiated by a light source with irradiance I1, some of the light will transfer through the film and appear on the other side with an irradiance I2. The ratio of the light transmitted through the material to the light from the source is defined as the transmissivity T or $$T = I2/I1. \qquad (1)$$

In the system described above, the light source 200 produces an average output irradiance $$I1 = K * A * D \qquad (2)$$

where
K = a constant for the source and geometry,
A = the peak current through the light source, and
D = the duty cycle of the current pulse which is pulse width divided by the pulse period.

The light impinging on the detector is given by $$I2 = T * I1 \qquad (3)$$

where
T = the transmissivity of the medium between the detector and the light source 200.

The detector 201 produces an output $$G = f(I2) \tag{4}$$

where
G = a detecting device property affected by the irradiance I2, e.g., resistance of a photo conducting detector, CdS or CdSe or reverse current of a photo diode, e.g., Si, and etc.
f(I2) is a function, usually nonlinear, dependent upon the detector characteristics.

In the system described, the operation is such as to maintain the output of the detector 201 at a constant value, i.e.:

$$G = f(I2) = a\ constant \tag{5}$$

from which $$I2 = a\ constant. \tag{6}$$

Since $$I2 = I1 * T \tag{7}$$

it follows that $$T = I2/(K * A * D). \tag{8}$$

Since I2, K and A are all constants, they can be replaced by another constant P where $$P = I2/(K * A) \tag{9}$$

from which $$T = P/D. \tag{10}$$

Simply stated, the transmissivity of the medium between the source and the detector is inversely proportional to the pulse width (see pulses 209D in FIG. 3) of the modulator in the configuration described above. Since the detector 201 is always operated at a fixed level, the detector characteristics do not enter into the determination of the transmissivity measurement.

In practice the constant P can readily be calibrated or determined by simply interposing nothing between the source and the detector. Under these conditions, the transmissivity is defined as one. Therefore the constant P is equal to the duty cycle measured under these conditions. Once the constant P has been determined, the measurement is essentially ratiometric, being the ratio of the duty cycle with nothing in the path to the duty cycle with the object to be measured in the path.

Since the measurement is a duty cycle measurement, the stability of the oscillator 211 driving the pulse width modulator 206 is not critical. This eliminates the dependence of the measurement on the stability of the oscillator 211.

Figure 5:
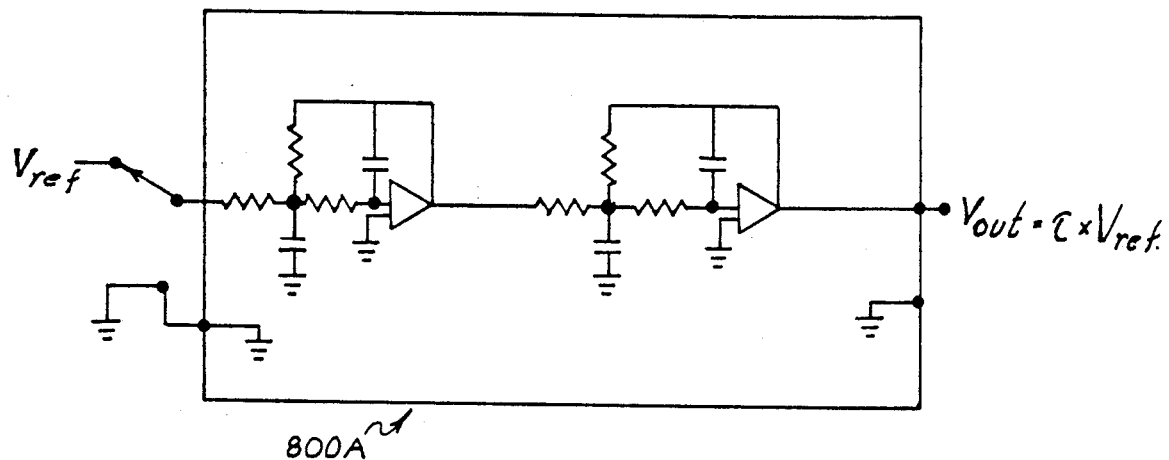
FIG. 5 shows schemically a typical duty cycle detector.

The pulse duty cycle measurement is readily made using techniques well known by those skilled in the art. For example, an analog voltage $V_{out}$ proportional to pulse duty cycle is readily obtained by arranging an electronic switch as in the duty cycle detector marked 800A in FIG. 5 that switches between a reference voltage $V_{ref}$ and ground under the control of the output pulse from the modulator. Filtering the resultant signal to remove the modulation frequency results in analog output $V_{out} = V_{ref}$ time the duty cycle which is directly proportional to duty cycle. FIG. 5 is self explanatory.

Since the output of the pulse width modulator 206 is a digital pulse, digital counting techniques, with their stability, can easily be employed to determine the duty cycle.

Figure 6:
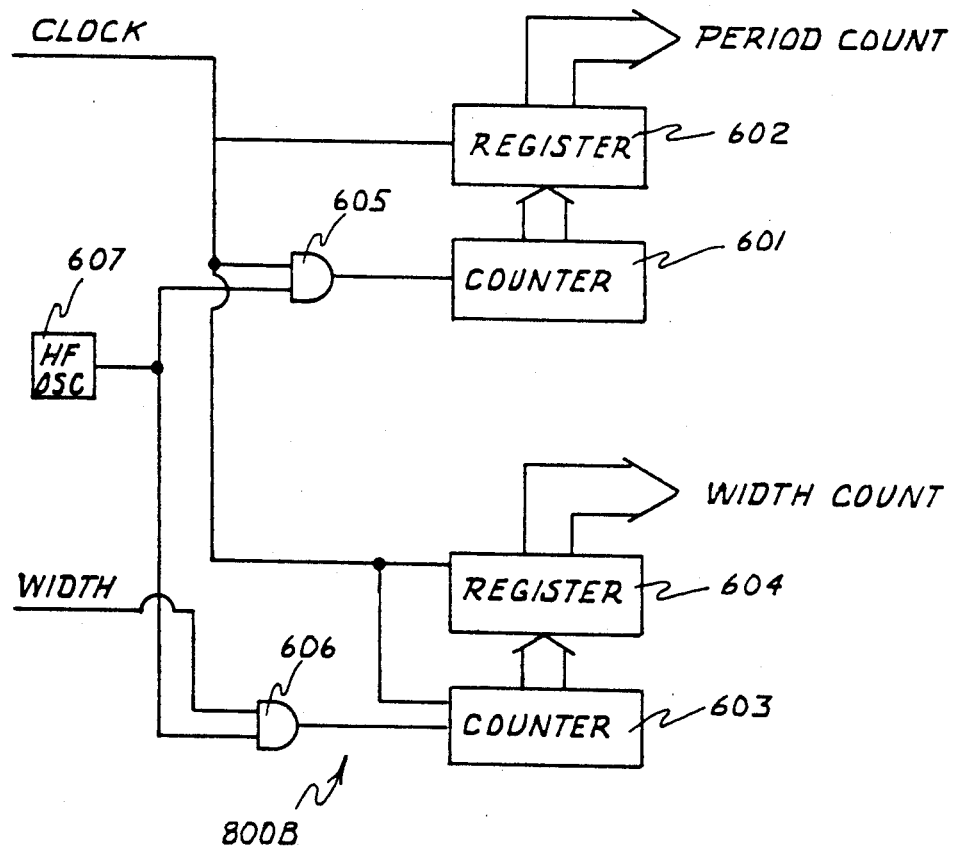
FIG. 6 shows diagrammatically a digital duty cycle detector.

FIG. 6 shows schematically a duty cycle detector 800B wherein two counters 601 and 603 can be used in conjunction with a high frequency oscillator 607. The counter 601 is gated to count pulses from the high frequency oscillator 607 throughout one entire period of the pulse-width oscillator labeled clock in the figure. At the conclusion of each period the contents of the counter 601 are transferred to a register 602 and the counter 601 is reset. The contents of the register 602 thus represent the number of high frequency pulses for the pulse-width oscillator period or one hundred percent duty cycle. A second counter 603 is arranged to count pulses from the same high frequency oscillator 607 for the duration of the pulse width-modulator under control of a gate 606. At the conclusion of each period the contents of this counter 603 are transferred to a second register 604 and the counter 603 is reset to zero. The contents of the register 604 thus represent the number of clock pulses for the pulse width. The ratio of the contents of register 604 to that of register 602 is then the duty cycle of the pulse width modulator. Since each of these registers can easily be read by a microprocessor, the computation of pulse duty cycle and hence optical transmissivity is readily carried out.

The description above discussed the conditions for a transmissive system. The apparatus described is equally suited for use in a reflective system. Under these conditions, a light source directs light with an irrandiance I1 onto an object which reflects some of the light with an irradiance I2 back to a detector. The ratio of the source light to the reflected light is defined as the reflectance R or $$R = I2/I1. \tag{11}$$

By an analysis similar to that for the transmissive case, the reflectance of the material irradiated by the modulated light source is given by $$R = P/D \tag{12}$$

where
P = the duty cycle for R = 1, and
D = the duty cycle of the current pulse.

In the reflective case, calibration is accomplished by inserting a material of known reflectivity into the test are and measuring the duty cycle obtained under these conditions. The constant P is thus determined to be equal to the known reflectivity times the duty cycle measured with the known reflector.

As discussed earlier, measuring the presence or position of thin laminating films can be difficult since they must be largely optically transparent by definition. However, most films are not uniformily transmissive (or reflective) across the full spectrum. If a region of the spectrum can be found where the film itself or the composite film is less transmissive, it is possible to operate the detection system over this region of the spectrum only and thus enhance the accuracy and reliability of the system. By choosing a light source and a detector that have a narrow spectral response centered at the wavelength of maximum contrast ratio for the film in question and matched to each other, the optimum level of performance can be obtained.

As an example of the efficacy and utility of the detector system, consider the problem of detecting the presence of a polyimide film on a silicone coated paper liner. At the IR end of the spectrum, the transmissivity of the polyimide film is approximately 90%. The transmissivity of the backing is similarly about 90%. The transmissivity of the film plus backing is about 80%. Using any conventional open loop detection scheme, drift and aging in the detector system would render reliable operation impossible.

Using the system of the present invention, the measured duty cycle with a material of transmissivity T interposed is given by $$D = P/T. \tag{13}$$

The difference in duty cycle obtained from two different materials of transmissivities T1 and T2 respectively is given by $$(D2 - D1) = P * (1/T1 - 1/T2) \tag{14}$$

or $$(D2 - D1) = P * ((T2 = T1)/(T2 * T1)). \tag{15}$$

For the materials described above, T2=0.9 and T1=0.08. Substituting these values, $$(D2 - D1) = P * (0/1)/(0.72). \tag{16}$$

If the constant P is set equal to 0.72, then the change in duty cycle for a change in duty cycle from 0.9 to 0.8 is 0.1 or 10%. Since the feedback loop guarantees the stability of the operating point of the detector system, it is possible to operate the system reliably even under these adverse conditions.

If the spectral characteristics of the light source and detector are shifted more towards the visible, the liner and film both become more opaque, the film to a lesser extent until the green end of the spectrum is reached. Under green irradiance, typical values for transmissivity are 0.3 for the liner, 0.6 for the film and 0.2 for the composite. The difference in transmissivity between the liner alone and the liner plus film is thus 0.3−0.1 as it was above. The difference in duty cycle for these values is given by $$\begin{aligned}(D2 - D1) &= P * (0.3 - 0.2)/(0.06) \\ &= P * 1.67\end{aligned} \tag{17}$$

Since the absolute duty cycle can never exceed one, the constant P must be chosen small enough to resolve the lowest transmissivity expected. In this case, Tmin=0.2 and hence the maximum value for P=0.2. In order not to saturate the system, if P is chosen equal to 0.1, then the difference in duty cycle between the two conditions of liner alone and liner plus film is $$\begin{aligned}(D2 = D1) &= 0.1 * 1.67 \\ &= 0.167\end{aligned} \tag{18}$$

or almost 17% change in duty cycle for a 10% change in absolute transmissivity.

The stability of the detector system permits reliable operation under the conditions of high attenuation and low contrast ratio. Optimizing the wavelength can improve the detectability of the system even though the attenuation of the light is greatly increased.

Figure 7:
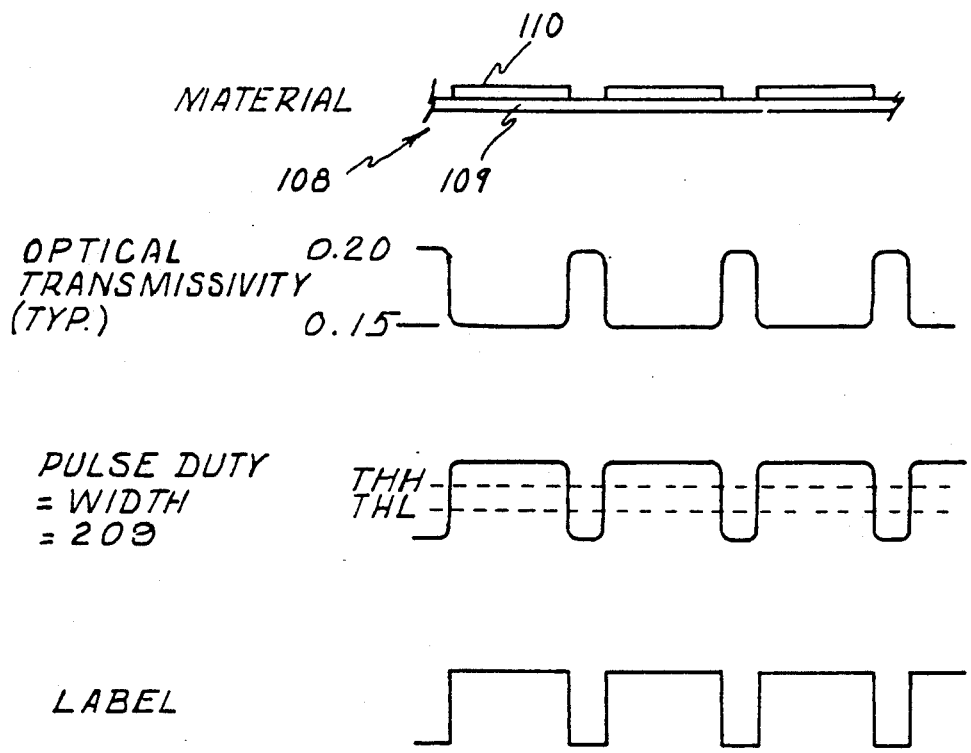
FIG. 7 shows a scheme to permit edge detection.

Referring back to FIG. 1, the sensor 101 detects the absolute transmissivity of the stock 108 that is in its path. FIG. 7 depicts the conditions of the detector as a function of the stock. The signal LABEL is generated in the controller 121 in FIG. 1 from the signal WIDTH at 209 by establishing two thresholds THH and THL, shown for example in FIG. 7. A duty cycle detector such as those shown respectively at 800A and 800B in FIGS. 5 and 6 is incorporated as part of the controller 121 and produces an output proportional to duty cycle. The controller 121 determines if the duty cycle is above the threshold THH, in which case the signal LABEL is set true, or if the duty cycle is below the threshold THL, in which case the signal LABEL is set false. The thresholds THH and THL are usually not equal, some hysteresis being employed to assure monotonicity and prevent oscillations at the threshold.

Since the detector system described is extremely sensitive, stable and accurate, it is possible to locate the edge 112 of the film 110 with great precision and hence control its placement on the head 124 of FIG. 1 with equal precision. As stated, the target label 125 in FIG. 1 can also be positioned accurately under the head 124, and hence the film 110 can be placed over the label 125 by firing the applicator arm 145 by the driver 145A using techniques well known in this art.

Figure 8:
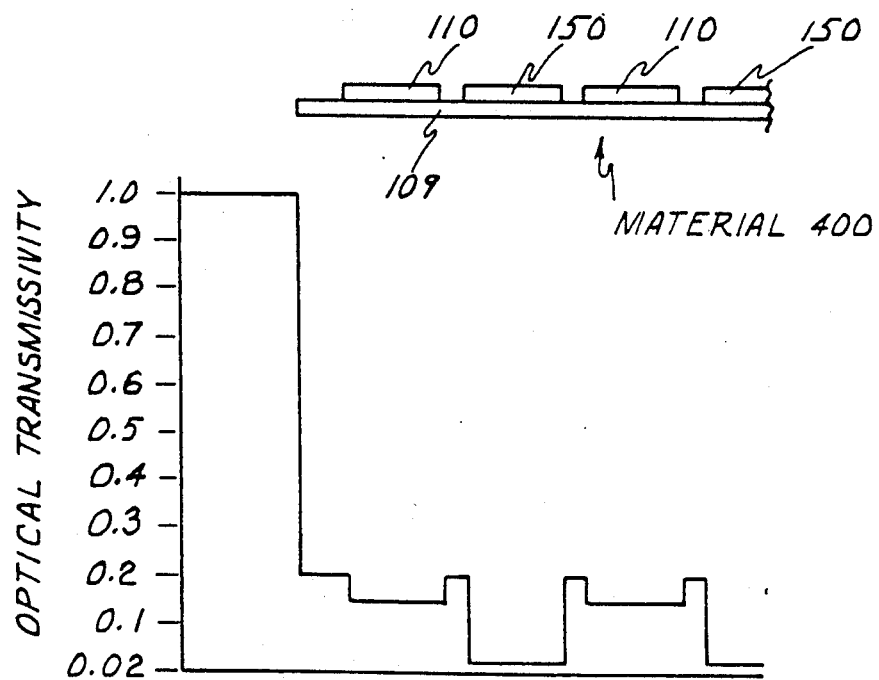
FIG. 8 shows a composite material and a graph representative of optical density at longitudinal regions of the composite material.

In another embodiment of the invention, a composite label material 400 in FIG. 8 is sued in conjuction with a printer applicator. Referring to FIG. 8, a backing material or carrier 109 serves to transport a printable label material 150 followed by a laminating film material again marked 110. The materials 150 and 110 are placed on the backing 109 alternately throughout its entire length. The label material 150 takes the place of the label material 125 discussed in the prior structure and shown in FIG. 1. FIG. 8 also shows the typical optical density of composite the material 400 described above.

Figure 9:
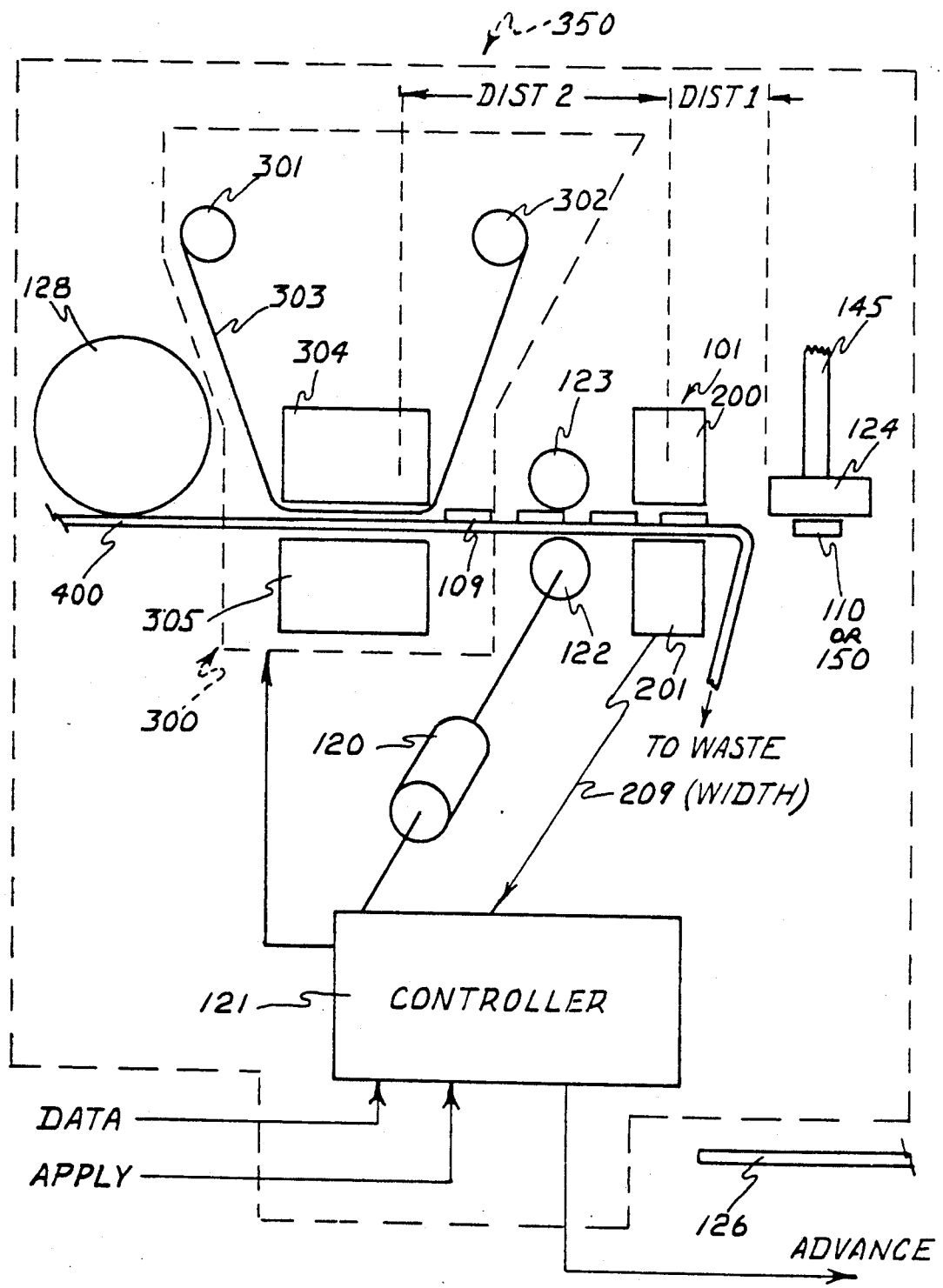
FIG. 9 shows diagrammatically a modification of the apparatus shown in earlier figures, and, in some cases, with different identifiers.

FIG. 9 shows a typical schematic of apparatus 350 that used the detector system 101 of this disclosure in conjunction with the composite material 400 of FIG. 8 to print, apply and laminate labels. The composite material 400 is contained on a supply reel again marked 128 that is loaded onto the printer applicator 350. A controller again marked 121 controls the operation of a printing station marked 300. The printing station 300 may be any type of printer suitable for printing labels, but is typically an impact type printer using a character forming mechanism 304, an image transfer mechanism 305, a ribbon 303 and a mechanism for transporting the ribbon between rolls 301 and 302. The use of an impact type printer is illustrative and not restrictive for the disclosure. Other means such as thermal transfer, electrostatic or ink jet could equally well be used. The controller 121 in FIG. 9 controls the position of the composite label stock 400 through a positioning motor 120 (for example a stepping motor operating in conjunction with a capstan 122 and pressure roller 123). A detector again marked 101 of the type described in this disclosure is located a known distance DIST1 from an applicator head again marked 124. The detector 101 is also located a known distance DIST2 from the print point of the printer 300. Operation of the positioning motor 120, the printer 300 and applicator 145 is controlled by the controller 121 in FIG. 9.

Figure 10:
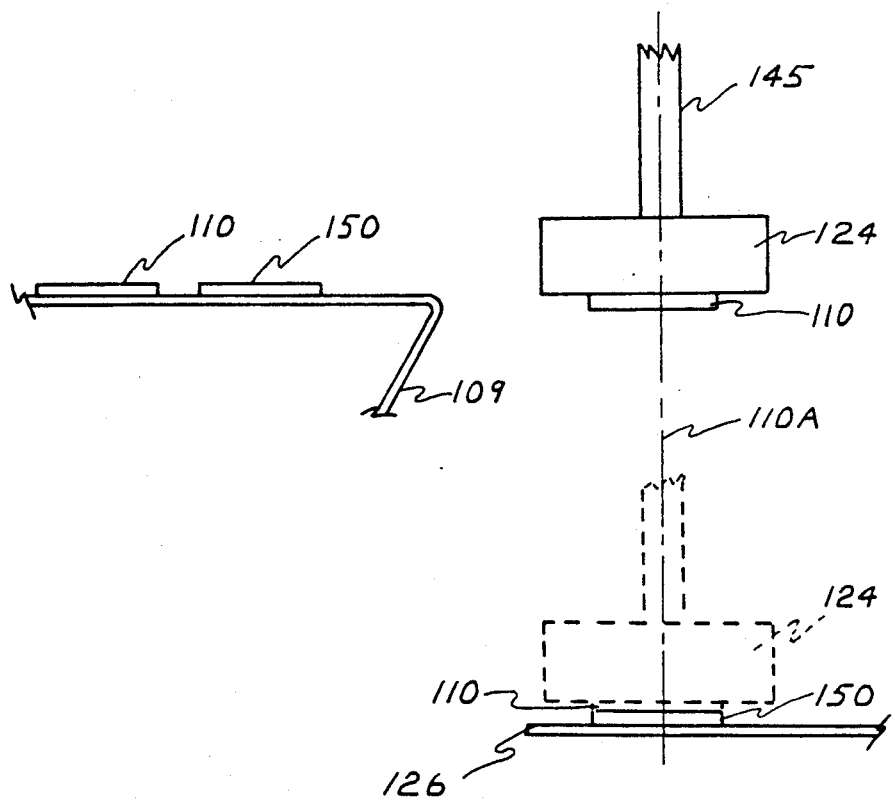

The controller 121 in FIG. 9 receives information to be printed from an external source shown as DATA in the figure. The controller 121 advances the composite label stock 400 through the machine and receives information from the detector system 101 as to the optical density of the material in its aperture. FIG. 8 shows a typical optical density of the composite material as it passes through the aperture of the detector 101. Since the detector system 101 provides a pulse-width signal to the controller 121 that is inversely proportional to optical transmissivity, the controller 121 can readily determine with a high degree of accuracy and stability the makeup of the material directly in its aperture at any given time. From this information and in conjunction with the known distances DIST1 to the strip point and DIST2 to the print point, in FIG. 9, the controller 121 can determine the label size, the film size and the absolute location of each. With this determination the controller 121 in FIG. 9 can now advance the stock through the machine causing the printer 300 to print data on the label stock 150 in FIG. 8 only and to skip past the laminating film 110. The controller 121 also advances a printed label 150 out onto the applicator head 124 and when it is completely in place on the head interrupts the stock advance process and applies it to the item 126 to be labeled. The controller 121 then resumes advancing the stock 400 printing or not as dictated by the relative position of the label material 150 with respect to the print point until the film material 110 has been completely positioned onto the head. The controller suspends the stock advance process and initiates an apply cycle. FIG. 10 shows this status. The second apply cycle results in the printed and applied label 150 being overlaminated with the film 110. Following this sequence the controller 121 issues a signal advance which informs the external positioning apparatus (not shown in the figures) that a complete cycle has been finished and the item to be labeled may be advanced and replaced by another for the next cycle.

A few matters are addressed in this paragraph. In FIG. 3 a transistor 207A serves to develop the signal WIDTH through the resistor 209B which provides a pulse-width-modulated signal at 209, the pulse at 209 being marked 209D and taking various widths, as earlier described.

Figure 11:
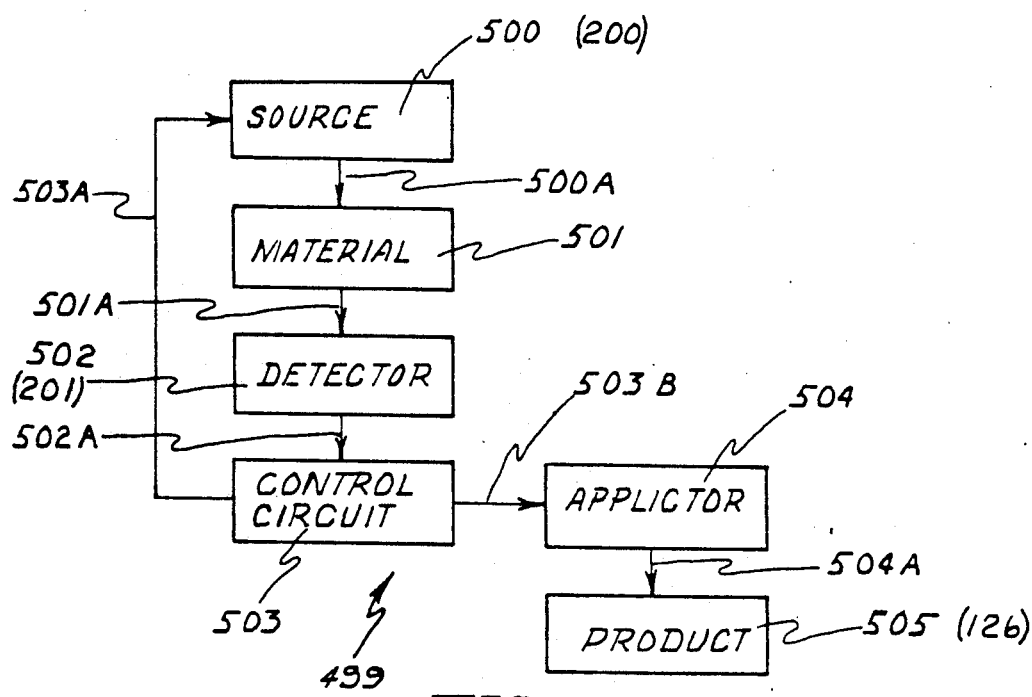

The apparatus designated 499 in FIG. 11 is a system for labeling which permits very precise positioning of labels onto the surface of a product 505 (like the product 126 in earlier figures; other elements in FIG. 11 that perform the same or similar functions to earlier described elements have 500-numbers applied and some corresponding numbers from earlier figures are shown in parentheses adjacent the 500-numbers; this should not cause any confusion), as well as protective covers or the like upon the labels. The system 499 includes a source 500 (see 200 in FIG. 3) of wave energy (e.g., electromagnetic radiation) which emanates therefrom at 500A. The source 500 is positioned to direct the wave energy at 500A onto a material 501 (like the material 108, for example) which effects a change in the intensity of the wave energy to give a resultant wave energy at 501A which has a particular intensity level, the resultant wave energy at 501A being indicative of the optical density of the material 501. The voltage signal at 502A is connected as input to a control circuit 503 (205, 206 plus other elements in FIG. 3) connected along a feedback path 503A (207 and 208 in FIG. 3) to the source 500, the performance characteristics of the control circuit 503 being chosen such that the control circuit 503 is operable in response to the voltage signal at 502A to modify the average output of the wave energy 500A of the source 500 to maintain substantially constant output at 502A from the source 500 through the material 501. As is noted above, the control circuit 503 employs circuitry to provide at 503A an output electric signal consisting of electric pulses that are binary in form and pulse-width modulated. The intensity of the source output at 500A is determined precisely by the duty cycle of the signal at 503A and the duty cycle is binary-digital in form—hense very stable and very precise. The duty cycle signal at 503A, also, and within the control circuit 503, functions to generate a signal (electric) at 503B to applicator 504, which signal is a direct measurement of a property of the material being sensed by the detector 502. The applicator 504 applies a mechanical signal 504A to apply a label or similar thin film onto the product 505. The applicator 504 includes a mechanism like the controller 121 in FIG. 1, that is responsive to the PWM-signal 503B, as well as 145A, etc. The important issue here is that it is the duty cycle of the signal at 503A that causes a signal at 503B that activates the applicator 504. The "measurement apparatus" referred to herein includes the source 500, the detector 502 and the control circuit 503. The use of the applicator example is illustrative of a typical use of the detector apparatus herein.

Modifications of the invention herein disclosed will occur to persons skilled in the art and all such modifications are deemed to be within the scope of the invention as defined by the appended claims.

What is claimed is:

1. Optical density measurement apparatus to measure the optical density of a composite material, that comprises:

a light source whose spectral characteristics are matched to the material to be measured, positioned to direct radiation onto the composite material which effects a change in the intensity of the radiation;

a detector whose optical characteristics are matched to the light source positioned to detect the radiation after interaction with the composite material and operable to generate a voltage signal indicative of the intensity level of the detected radiation; and a control circuit whose output is connected to energize the light source and being interconneted to receive the voltage signal, the performance characteristics of the control circuit being chosen such that the control circuit is operable in response to the voltage signal to modify the average output of the light source to maintain the voltage output of the detector substantially constant, the control circuit being pulse-width modulated to effect modification of the average output of the light source to maintain substantially constant output from the detector by varying the average output from the light source in response to the voltage signal, the light source being one that can be modulated to produce an average light output that is proportional to the peak output of the control circuit output times the duty cycle of the control circuit output, said duty cycle being a direct measure of said optical density.

2. Optical density measurement apparatus according to claim 1 in which the positional geometry of the light source and the detector are such that the radiation from the light source is reflected from the material onto the detector nd is used to generate the control circuit output whose duty cycle is a direct measure of said optical density.

3. Optical density measurement apparatus according to claim 1 in which the positional geometry of the light source and the detector are such that the radiation from the light source is transmitted through the material onto the detector and is used to generate the control circuit output whose duty cycle is a direct measure of said optical density.

4. A system that includes the optical measurement apparatus of claim 1 and that further includes a mechanism to determine changes in the optical density and to react in response to changes in the optical density.

5. A system according to claim 4 that includes an applicator that is actuated in response to an edge between materials of differing optical density, which is connected to receive an actuation signal representative of said changes in the optical density of the composite, and which is actuated by the actuation signal.

6. A system that includes optical density measurement apparatus to measure optical density of a composite material, said optical density measurement apparatus comprising a light source positioned to direct radiation onto the composite material which effects a change in the intensity of the radiation;
   a detector whose optical characteristics are matched to the light source positioned to detect the radiation after interaction with the composite material and operable to generate a voltage signal indicative of the intensity level of the detected radiation;
   a control circuit connected to energize the light source and being interconnected to receive the voltage signal, the performance characteristics of the control circuit being chosen such that the control circuit is operable in response to the voltage signal to provide a control circuit output operable to modify the average output of the light source and hence maintain the voltage output of the detector substantially constant, the control circuit being pulse-width modulated to effect modification of the average output of the light source to maintain substantially constant output from the detector by varying the average output from the light source in response to the voltage signal, which control circuit output is a direct measure of optical density; and
   a mechanism to determine changes in the optical density and to react in response to changes in the optical density.

7. The system of claim 6 in which the positional geometry of the light source and the detector are such that the radiation from the light source is reflected from the material onto the detector.

8. A system according to claim 7 that includes an applicator that is actuated in response to an edge between materials of differing optical density, which is connected to receive an actuation signal representative of said changes in the optical density of the composite and which is operable to apply with great precision a thin film onto an object in response to said activation signal.

9. A system for very precise positioning of a thin film derived from a composite material upon a surface that comprises:
   optical density measurement apparatus to measure the optical density of the composite material, said optical density measurement apparatus comprising a light source whose spectral characteristics are matched to the composite material to-be measured, positioned to direct radiation onto the composite material which effects a change in the intensity of the radiation;
   a detector whose optical characteristics are matched to the light source positioned to detect the radiation after interaction with the composite material and operable to generate a voltage signal indicative of the intensity level of the detected radiation;
   a control circuit connected to energize the light source and being interconnected to receive the voltage signal, the performance characteristics of the control circuit being chosen such that the control circuit is operable in response to the voltage signal to modify the average output of the light source to maintain the voltage output of the detector substantially constant, the control circuit output being pulse-width modulated to effect modification of the average output of the light source to maintain substantially constant output from the detector by varying the average output from the light source in response to the voltage signal, the light source being one that can be modulated to produce average light output that is proportional to the peak output of the control circuit output times the duty cycle of the control circuit output, said duty cycle being a measure of said optical density; and
   a mechanism connected to receive said control circuit output and to be controlled thereby to react in response to changes in the optical density reflected in the control circuit output to apply the thin film onto the surface at a precise location on the basis of said control circuit output.

10. The system of claim 9 in which the positional geometry of the light source and the detector are such that the radiation from the light source is reflected from the material onto the detector.

11. A system according to claim 9 in which said mechanism to react includes an applicator that is actuated in response to an edge between materials differing optical density in said composite, which applicator is connected to receive an actuation signal representative of said changes in the optical density of the composite, and which serves to apply the thin film upon the surface.

12. Optical density apparatus according to claim 1 in which the pulse-width of the voltage signal is derived from a digital pulse derived using digital counting techniques, with their stability, to determine the duty cycle of said average output.

13. Optical density measurement apparatus to measure the transverse optical density of a composite material, that comprises:
   a light source positioned to direct radiation in the transverse direction onto the composite material which effects a change in the intensity of the radiation;
   a detector positioned to detect the radiation after interaction with the composite material and operable to generate a feedback voltage signal indicative of the intensity level of the detected radiation received after said interaction; and a control circuit connected to energize the light source and being interconnected to receive the feedback voltage signal, the performance characteristics of the control circuit being chosen such that the control circuit output is operable in response to the feedback voltage signal to modify the average output of the light source and to maintain the voltage output of the detector substantially constant in time, the control circuit being pulse-width modulated to effect modification of the average output of the light source to maintain substantially constant output from the detector as a function of time by varying the average output from the light source in response to the feedback voltage signal, the light source being one that can be modulated to produce average light output that is proportional to the peak output of the control circuit output times the duty cycle of the control circuit output, said duty cycle being a direct measure of said optical density.

14. Measurement apparatus to measure a characteristic of a material, that comprises:

a source of electromagnetic radiation positioned to direct radiation onto the material which effects a change in the intensity of the radiation;

a detector positioned to detect the radiation after interaction with the material and operable to generate a voltage signal indicative of the intensity level of the detected radiation; and a control circuit connected to energize the source and being interconnected to receive the voltage signal, the performance characteristics of the control circuit being chosen such that the control circuit output is operable in response to the voltage signal to modify the average output of the source to maintain the voltage output of the detector substantially constant in time, the control circuit being pulse-width modulated to effect modification of the average output of the source to maintain substantially constant output from the detector as a function of time by varying the average radiation output from the source in response to the voltage signal, the light source being one that can be modulated to produce average light output that is proportional to the peak output of the control circuit output times the duty cycle of the control circuit output, said duty cycle being a direct measure of said optical density.

15. Measurement apparatus according to claim 14 in which the source irradiates the composite material with radiation in the visible region of the electromagnetic spectrum.

16. Measurement apparatus according to claim 15 in which the intensity of the source of electromagnetic radiation is controlled by pulse-width modulation techniques to produce an output irradiance I1, where $$I1 = K * D * A$$

where
K = a constant for the source and geometry,
A = the peak current through the light source, and
D = the duty cycle of the current pulse
which is the pulse-width divided by the pulse period.

17. Measurement apparatus according to claim 16 in which the control circuit embodies digital structures which employ digital counting techniques, with their inherent stability, to measure the duty cycle.

18. A system that includes the measurement apparatus of claim 17 and then further includes an applicator adapted to apply a thin film precisely upon an object, which applicator is energized by structures that react to said duty cycle.

19. A system that includes measurement apparatus to measure a characteristic of a material, that comprises:

a source of wave energy positioned to direct the wave energy onto the material, which material effects a change in the intensity of the radiation;

a detector positioned to detect the wave energy after interaction with the material and operable to generate a voltage signal indicative of the intensity level of the detected wave energy; and a control circuit connected to energize the source of wave energy and being interconnected to receive the voltage signal, the performance characteristics of the control circuit being chosen such that the control circuit is operable in response to the voltage signal to modify the average output of the source to maintain the voltage signal output of the detector substantially constant, the control circuit output being pulse-width modulated to effect modification of the average output of the source to maintain substantially constant the voltage signal output from the detector by varying the average output of the wave energy from the source in response to the voltage signal, said source being one that can be modulated to produce average wave energy output that is proportional to the peak of the output times the duty cycle of the control circuit output, said duty cycle being a direct measure of said characteristic, said system further including an applicator operable to apply a thin film precisely upon an object, which applicator is energized by structures that react and are controlled in response to the duty cycle of said control circuit output.

20. A method of measuring a characteristic of a material, that comprises:

directing electromagnetic wave energy from a linear source of such wave energy onto the material, which material effects a change in the intensity of the radiation;

detecting the wave energy after interaction with the material and generating a voltage signal indicative of the intensity level of the detected wave energy;

providing a pulse-width modulated control circuit connected to energize the source of the electromagnetic wave energy and being interconnected to receive the voltage signal, the duty cycle of the control circuit itself being a measure of said characteristic; and providing performance characteristics of the control circuit to provide an average response of the control circuit to the voltage signal which maintains said voltage signal substantially constant by varying the average output of the electromagnetic wave energy from the source of electromagnetic wave energy in response to the control circuit output, said source being one that can be modulated to produce average light output that is proportional to the peak output of the control circuit output times the duty cycle of the control circuit output.

21. A method according to claim 20 in which the pulse-width modulated control circuit is operable to provide an output electric signal in the form of electric pulses that are binary in form, are pulse-width modulated and serve to energize said source and control the output thereof.

22. A method according to claim 21 that further includes providing an applicator to apply a label onto a product, which applicator is activated by a binary pulse-width-modulated signal from said control circuit.

23. Apparatus according to claim 1 in which the light source is one of a gas discharge tube, a light emitting diode and an electro-luminescent device.

24. A binary-directed system for very precise positioning of a thin film derived from a composite material upon a surface, that comprises:

optical measurement apparatus to measure an optical characteristic of the composite material, said optical measurement apparatus comprising a light source positioned to direct radiation onto the composite material, which material effects a change in the radiation;

a detector system positioned to detect the radiation after interaction with the composite material and operable to generate a voltage signal indicative of the characteristic of the detected radiation;

a control circuit connected to energize the light source and being interconnected to receive the voltage signal, the performance characteristics of the control circuit being chosen such that the control circuit is operable in response to the voltage signal to modify the average output of the light source to maintain the voltage output of the detector substantially constant, the control circuit output being binary in form and being pulse-width modulated to effect modification of the average output from the detector by varying the average output from the light source in response to binary pulse-width modulated control circuit output, the light source being one that can be modulated to produce average light output that is proportional to the peak output of the control circuit output times the duty cycle of the control circuit output, said duty cycle being a measure of said optical characteristic; and a mechanism to react in response to changes in the optical density as reflected or found in the control circuit output to apply with great positional accuracy the thin film onto the surface.

25. A system according to claim 19 in which the measurement of material characteristic is essentially ratiometric, being the ratio of the duty cycle of the control circuit output with unit optical characteristic divided by the duty cycle determined in connection with the material whose characteristic is to be measured.

* * * * *